(12) United States Patent
Dubois et al.

(10) Patent No.: US 6,455,746 B1
(45) Date of Patent: Sep. 24, 2002

(54) ULTRAFINE POLYMETALLIC PARTICLES, PREPARATION AND USE FOR HYDROGENATING OLEFINS AND FOR COUPLING HALOGENATED AROMATIC DERIVATIVES

(75) Inventors: Jean-Marie Dubois, Pompey; Yves Fort, Vandoeuvre les Nancy; Olivier Tillement, Froloy, all of (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/509,003

(22) PCT Filed: Sep. 15, 1998

(86) PCT No.: PCT/FR98/01967

§ 371 (c)(1),
(2), (4) Date: Mar. 21, 2000

(87) PCT Pub. No.: WO99/15271

PCT Pub. Date: Apr. 1, 1999

(30) Foreign Application Priority Data

Sep. 23, 1997 (FR) ............................................ 97 11814

(51) Int. Cl.⁷ ........................... C07C 7/163; C07C 5/02; B22F 1/00; B22F 9/16
(52) U.S. Cl. ........................ 585/258; 585/259; 585/260; 585/250; 585/422; 585/425; 75/351; 75/362; 75/370; 75/371; 75/373; 75/374; 75/255
(58) Field of Search .................................. 585/258, 259, 585/260, 250, 422, 425; 75/351, 362, 370, 371, 373, 374, 255

(56) References Cited

U.S. PATENT DOCUMENTS

| | | | | |
|---|---|---|---|---|
| 2,687,951 A | * | 8/1954 | Whaley | 75/370 |
| 3,180,835 A | * | 4/1965 | Peri | 516/33 |
| 3,814,696 A | * | 6/1974 | Verdone et al. | 516/33 |
| 4,111,686 A | * | 9/1978 | Paris et al. | 75/344 |
| 4,713,110 A | * | 12/1987 | Bogdanovic et al. | 75/370 |
| 4,863,510 A | * | 9/1989 | Tamemasa et al. | 75/370 |
| 5,147,841 A |   | 9/1992 | Wilcoxon | |
| 5,308,377 A | * | 5/1994 | Bonnemann et al. | 75/351 |
| 5,332,646 A | * | 7/1994 | Wright et al. | 430/137 |
| 5,385,716 A | * | 1/1995 | Bogdanovic et al. | 423/463 |
| 5,498,402 A | * | 3/1996 | Bogdanovic et al. | 423/463 |
| 5,872,074 A | * | 2/1999 | Schulz et al. | 502/328 |
| 5,925,166 A | * | 7/1999 | Viau et al. | 75/369 |
| 5,951,739 A | * | 9/1999 | Klapdor et al. | 75/371 |
| 6,103,868 A | * | 8/2000 | Heath et al. | 528/482 |

FOREIGN PATENT DOCUMENTS

| | | |
|---|---|---|
| DE | 44 43 705 | 6/1996 |
| EP | 0 522 669 A2 | 1/1993 |
| WO | WO 97/33690 | 9/1997 |

OTHER PUBLICATIONS

Brunet et al., *J. of Org. Chemistry*, 1980, vol. 45, No. 10, pp. 1937–1945.
Haber et al., "Chemical Synthesis of Nanocrystalline Titanium and Nickel Aluminides from the Metal Chlorides and Lithium Aluminum Hydride," Advanced Materials, 1996, 8, No. 2, pp. 163–66.
Schwab et al., "Chemical Synthesis and Characterization of Nanosized Titanium Aluminide," Materials Science & Engineering, A204 (1995), pp. 197–200.

* cited by examiner

*Primary Examiner*—Walter D. Griffin
(74) *Attorney, Agent, or Firm*—Burns, Doane, Swecker & Mathis, L.L.P.

(57) ABSTRACT

The invention concerns ultrafine polymetallic particles obtained from reducing a mixture of salts dissolved in an organic solvent by an alkali or alkaline earth metal hydride, at a temperature not higher than the solvent reflux temperature, the mixture of dissolved salts comprising at least a salt of a metal having a standard oxidant potential $E°_{M^{n+}/M}$ at 25° C. higher than −1.18 V. The invention is applicable to the hydrogenation of olefins and the coupling of halogenated aromatic derivatives.

27 Claims, 5 Drawing Sheets

Fig. 5

ULTRAFINE POLYMETALLIC PARTICLES, PREPARATION AND USE FOR HYDROGENATING OLEFINS AND FOR COUPLING HALOGENATED AROMATIC DERIVATIVES

BACKGROUND OF THE INVENTION

1. Field of the Invention

A subject-matter of the present invention is a process for the preparation of ultrafine polymetallic particles, the particles obtained and the use of the particles obtained, in particular in catalysis.

2. DESCRIPTION OF THE RELATED ART

Fine metallic particles are known in various applications, in particular in catalysis. Various processes for preparing them have been disclosed.

L. K. Kurihara, et al. (Nanostructured Materials, vol. 5, No. 6, 607–613, 1995) discloses the preparation of nanometric particles of a metal by a so-called "polyol" process employed for various easily reducible metals, such as, for example, Fe, Co, Ni, Cu, Ru, Rh, Pd, Ag, Sn, Re, W or Pt, alone or as a mixture. Such a process consists in dissolving or suspending a precursor of the said metal in a polyol and in then heating at reflux in order to obtain a precipitate of metallic particles. The particles obtained can be nanometric. They are polymetallic when the reaction medium comprises salts of different metals. The use of a precursor salt of aluminum or of another metal which is difficult to reduce is not mentioned. For metals other than noble metals, the dimensions of the crystallites of the particles are greater than or equal to 8 nm, more generally between 10 and 80 nm. Only Ru and Pt make it possible to obtain lower mean crystallite dimensions, respectively of 5 and 2 nm. The production of nanometric Cu-Co particles is disclosed in L. K. Kurihara et al., J. Mat. Res., vol. 10, No. 6, June 1995. In this case, two metals are involved having a standard oxidation potential between −1.20 V and +0.8 V, that is to say easily reducible metals. The so-called "polyol" process does not make it possible, however, to prepare fine particles of a metal which is difficult to reduce, such as aluminum, for example.

Nanometric particles comprising aluminum can be prepared by reducing a salt with LiAlH$_4$. Thus, the preparation of nanocrystalline Ti/Al and Ni/Al particles from a chloride of the corresponding metal in the presence of LiAlH$_4$ is disclosed by J. A. Haber et al. (Advanced Materials, 1996, 8, No. 2). As the reaction mechanism of this process is as follows:

the Al content exhibits an upper limit corresponding to the valency of the associated metal. In addition, the structure of the powders obtained is difficult to control, the kinetics of decomposition of AlH$_3$ not being easy to predict.

In addition, the preparation of nanometric intermetallic particles using borohydrides is known. S. T. Schwab et al. (Materials Science and Engineering, A204 (1995), 197–200) describe the preparation of intermetallic particles by reduction of a mixture of salts of different metals with a borohydride (for example, TiCl$_4$+AlCl$_3$+lithium triethylborohydride) This process makes it possible to obtain intermetallic particles without limitation with regard to the contents of the respective metals. Nevertheless, it requires a heat treatment at 1000° C. in order to decompose the products obtained by reaction of the salts with the borohydride and to obtain the metallic forms.

Other processes are known which consist in reducing metal salts either with a borohydride or with an alkaline hydride activated by addition of BF$_3$. In all cases, the presence of boron in the reaction medium introduces a risk of pollution.

The preparation of fine monometallic particles by reaction of a metal salt with sodium hydride in solution in an organic solvent and in the presence of an alkoxide is also known. Such a process has been described for nickel particles and for zinc particles (Paul Caubere et al., J. Am. Chem. Soc., 1982, 104, 7130; P. Gallezot, C. Leclercq, Y. Fort and P. Caubere, Journal of Molecular Catalysis, 93 (1994) 79 83, pp. 80–83; Brunet et al., Journal of Organic Chemistry, 1980, vol. 45, pp. 1937–1945). The particles obtained have a crystallite dimension of the order of an nm and are of use in particular as catalysts for heterogeneous catalyses. When they are prepared in the presence of a phosphine or 2,2'-bipyridine ligand, they lose their reducing properties and behave as a coupling agent (Lourak et al., Journal of Organic Chemistry, 1989, vol. 54, pp. 4840–4844).

An analogous process has also been described for the preparation of monometallic Pd particles, which can be used as catalyst for hydrogenating acetylene (J. J. Brunet and P. Caubere, J. Org. Chem., 1984, 49, 4058–4060).

This process is particularly advantageous but cannot be effectively used to prepare particles of a metal which is difficult to reduce having a standard oxidation potential at 25° C. of less than −1.20 V, such as aluminum, for example. Furthermore, the reduction of an Al$^{3+}$ cation in the presence of sodium hydride or lithium hydride has never been touched on in these processes.

The usefulness of ultrafine polymetallic particles as catalyst in various reactions is known, in particular those which comprise aluminum or another metal, the salts of which are difficult to reduce. In point of fact, the processes of the prior art do not make it possible easily to obtain ultrafine polymetallic particles comprising aluminum of good purity and with no limitation on the aluminum content. The aim of the present invention is to provide such a process.

SUMMARY OF THE INVENTION

The present inventors have now found that, although the reduction of an aluminum salt with lithium hydride or sodium hydride gives ultrafine particles of metallic aluminum which rapidly reoxidize in the reaction medium, it is possible to obtain stable polymetallic particles comprising aluminum and another metal, there being no restriction on the Al content, by reduction of a mixture of salts with an alkali metal or alkaline earth metal hydride.

A subject-matter of the present invention is thus a process for the preparation of ultrafine polymetallic particles, the particles obtained and their uses.

The process of the present invention is a process for the preparation of ultrafine polymetallic particles by reduction of a mixture of salts in solution in an organic solvent using an alkali metal or alkaline earth metal hydride at a temperature of less than or equal to the reflux temperature of the solvent. It is characterized in that the mixture of salts in solution comprises at least one salt of a metal having a standard oxidation potential E°$_{M^{n+}/M}$ at 25° C. of greater than −1.18 V.

In a preferred embodiment of the invention, the mixture of salts which is reacted with the hydride additionally comprises at least one salt of a metal having a standard oxidation potential E°$_{M^{n+}/M}$ at 25° C. of less than −1.20 V.

The process is advantageously carried out by adding, to the reaction medium, an alkali metal, alkaline earth metal or transition metal aliphatic or aromatic alkoxide or an alkali metal, alkaline earth metal or transition metal aminoalkoxide. The addition of such an alkoxide has the effect of activating the reaction in which the metal ions are reduced by the hydride.

The salts used in the process of the present invention can be chosen from halides. They can also be chosen from organic salts, such as acetates or acetylacetonates, or from alkoxides.

The salt of a metal having a standard oxidation potential $E°_{M^{n+}/M}$ at 25° C. of less than −1.20 V (that is to say, the salt of a metal which is difficult to reduce) is a salt of a metal chosen from the group consisting of V, Zr, Ce, Ti, Hf and Al. The aluminum salts are particularly advantageous.

The salt of a metal having a standard oxidation potential $E°_{M^{n+}/M}$ at 25° C. of greater than −1.18 V (that is to say, the salt of a metal which is easier to reduce) is a salt of a metal chosen from the group consisting of Ni, Co, Fe, Cu, Zn, Cd, Cr, Mn, Pd, Ag, Pt, Au, Bi and Sb. Among these metals, Pd, Ag, Pt and Au, which have a standard oxidation potential $E°_{M^+/M}$ at 25° C. of greater than +0.8 V, are very easy to reduce.

The relative amounts of the various salts used in the reduction reaction are chosen as a function of the composition desired for the final polymetallic particles, it being understood that these proportions are retained during the reduction reaction.

The reducing agent used in the process of the invention is an alkali metal or alkaline earth metal hydride. Mention may be made, among these hydrides, of: LiH, NaH, KH, $CaH_2$ and $MgH_2$. LiH and NaH are particularly preferred.

NaH can advantageously be used in the form of a 65% by mass commercial solution in mineral oil, optionally after washing with an aprotic organic solvent.

Use may be made, as lithium hydride, of a commercial lithium hydride in powder form.

The hydride can be activated by the presence of an alkoxide or aminoalkoxide. Sodium tert-butoxide, lithium tert-butoxide, aluminum isopropoxide and sodium N,N-dimethylaminoethoxide are particularly preferred. The alkoxide is preferably formed in situ by the action of the hydride on an aliphatic or aromatic alcohol preferably chosen from the group consisting of tert-butanol, 2-methyl-2-pentanol, phenol, diethylene glycol monoethyl ether, neopentanol, cyclohexanol, ethanol and isopropanol.

The amount of hydride (as number of moles) which is added to the medium must be at least equal to the sum of the valencies of the metal cations to be reduced. When it is desired to activate the reduction by an alkoxide prepared in situ, it is necessary to increase the initial amount of hydride by the amount corresponding at least to the stoichiometry of the reaction in which the alkoxide is formed. A hydride excess is desirable, preferably of the order of 20%.

The reduction of the metal salt by the alkali metal or alkaline earth metal hydride is carried out in an aprotic organic solvent. The solvent can be chosen from aprotic ethers, aliphatic hydrocarbons or aromatic hydrocarbons. A mixture of several solvents can be used. The following solvents are mentioned by way of example: tetrahydrofuran, 1,2-dimethoxyethane, anisole, hexane, heptane, octane, benzene, toluene, xylene or mesitylene. It is preferable to use predistilled, purified and dried solvents which are free from peroxides.

The process of the present invention can also be carried out in the presence of a compound comprising a nitrogen-comprising or phosphorus-comprising ligand. Mention may be made, among nitrogen-comprising ligands, of bipyridines (for example, 2,2'-bipyridine, dialkylpyridines and dialkoxypyridines) and terpyridines (for example, 2,2',6,6'-terpyridine).

Mention may be made, among phosphorus-comprising ligands, of triphenylphosphine, 1,2-bis(diphenylphosphino)ethane, alkylphosphines and arylphosphines.

In carrying out the process, the reactants are dispersed in the organic solvent. In one embodiment of the process, all the reactants are introduced simultaneously into the reactor. In another embodiment, the reactants are introduced successively into the reactor, the order of introduction not being critical.

The reaction in which the mixture of salts is reduced can be carried out at any temperature within the range limited by the solidifying temperature and by the reflux temperature of the solvent used. It is particularly advantageous to carry out the reaction at the reflux temperature of the solvent when the reaction medium comprises a salt of a metal having a low reduction potential.

The progress of the reaction can be monitored by measuring the amount of hydrogen given off due to the reduction of the metal salts and, if appropriate, to the formation in situ of the alkoxides intended to activate the hydride.

The material obtained by the process provided is composed of nanometric polymetallic particles having a mean crystallite dimension of less than 4 nm and an intimate association of the various metals present inside the grains, which particles are composed of at least one metal chosen from the group consisting of Ni, Co, Fe, Cu, Zn, Cd, Cr, Mn, Pd, Ag, Pt, Au, Bi and Sb and of at least one metal chosen from the group consisting of V, Zr, Ce, Ti, Hf and Al. A material composed of particles comprising at least 70% by number of Al atoms is particularly preferred.

The particles obtained at the end of the reduction reaction can be used directly in the solvent in which they were obtained. It is also possible to remove the said solvent in order to obtain particles in powder form. When a heat treatment is desired, it can be carried out either before removing the solvent or on the powders obtained after removing the solvent.

The particles of the present invention exhibit catalytic properties in numerous reactions. They are particularly effective as hydrogenation catalyst and as catalyst for the direct coupling of halogenated aromatic derivatives. Their yield and their reaction rate are markedly greater than those of the monometallic particles used to date. It has been found, surprisingly, that the addition of Al, which has no catalytic activity, to a metal having an intrinsic catalytic activity increases the overall catalytic activity.

The present invention is illustrated hereinbelow by examples in which the catalytic performances of polymetallic particles obtained by the process according to the invention are compared with those of monometallic particles obtained by a similar process.

Figure 1:
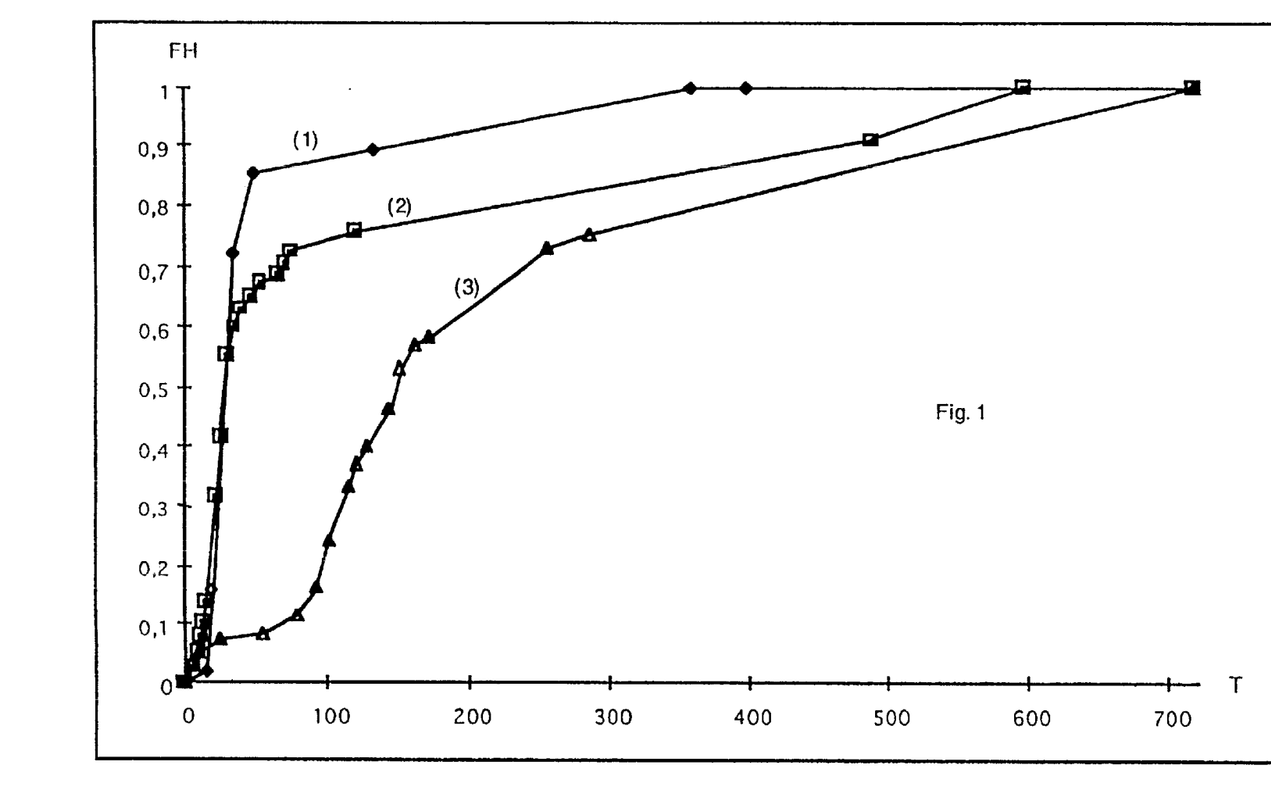
FIG. 1 of the Drawing graphically represents the fraction by volume of hydrogen given off as a function of time in regard to Examples 1 to 3.

In the appended figures:

FIG. 1 represents the fraction by volume FH of hydrogen given off as a function of the time T (expressed in minutes)

for the reaction of Example 1 (curve 1), of Example 2 (curve 2) and of Example 3 (curve 3).

Figure 2:
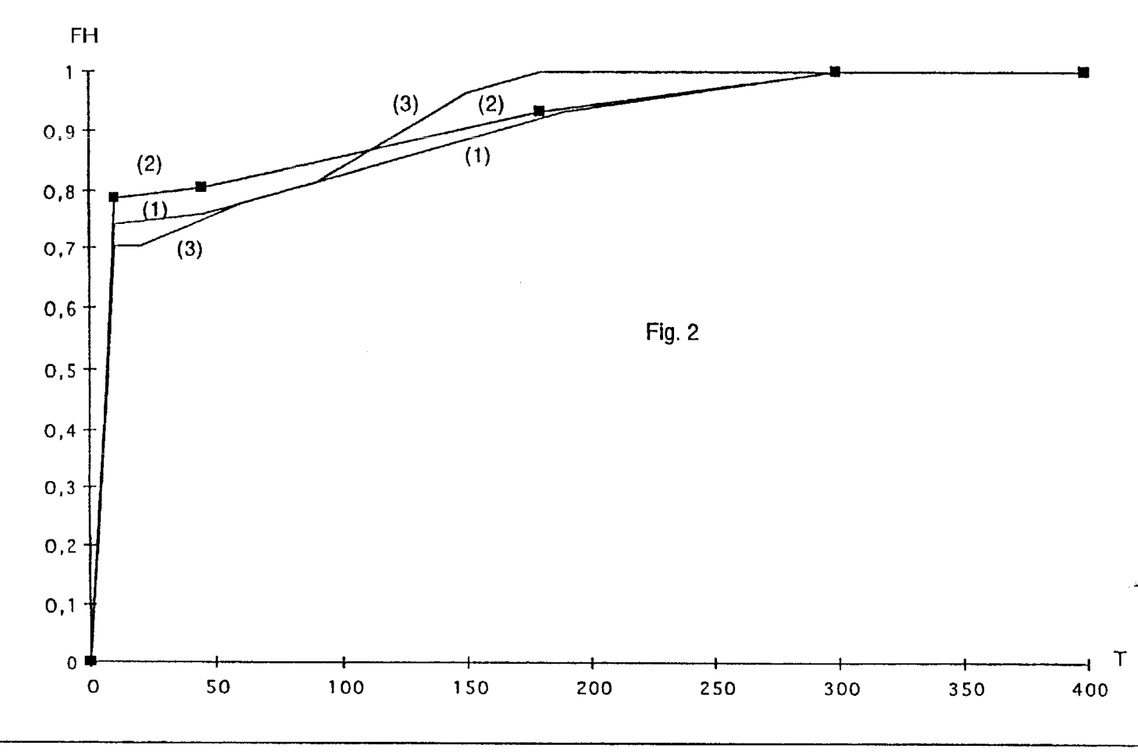
FIG. 2 of the Drawing graphically represents the fraction by volume of hydrogen given off as a function of time in regard to Examples 4 to 6.

FIG. 2 represents the fraction by volume FH of hydrogen given off as a function of the time T (expressed in minutes) for the reaction of Example 4 (curve 1), of Example 5 (curve 2) and of Example 6 (curve 3).

Figure 3:
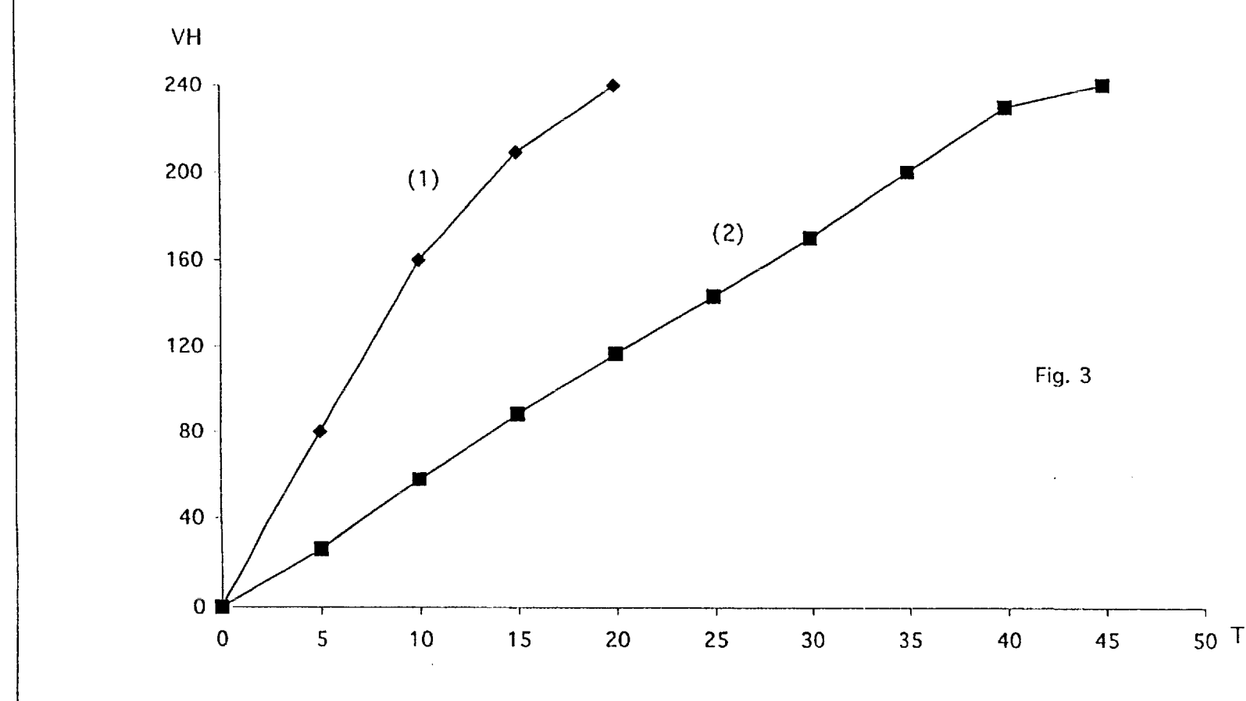
FIG. 3 of the Drawing graphically represents the variation in the volume of hydrogen consumed as a function of time during a styrene hydrogenation reaction.

FIG. 3 represents the curve showing the variation in the volume of hydrogen consumed VH (expressed in ml) as a function of the time interval T (expressed in minutes) during a styrene hydrogenation reaction catalyzed by AlNi particles (curve 1) and Ni particles (curve 2).

Figure 4:
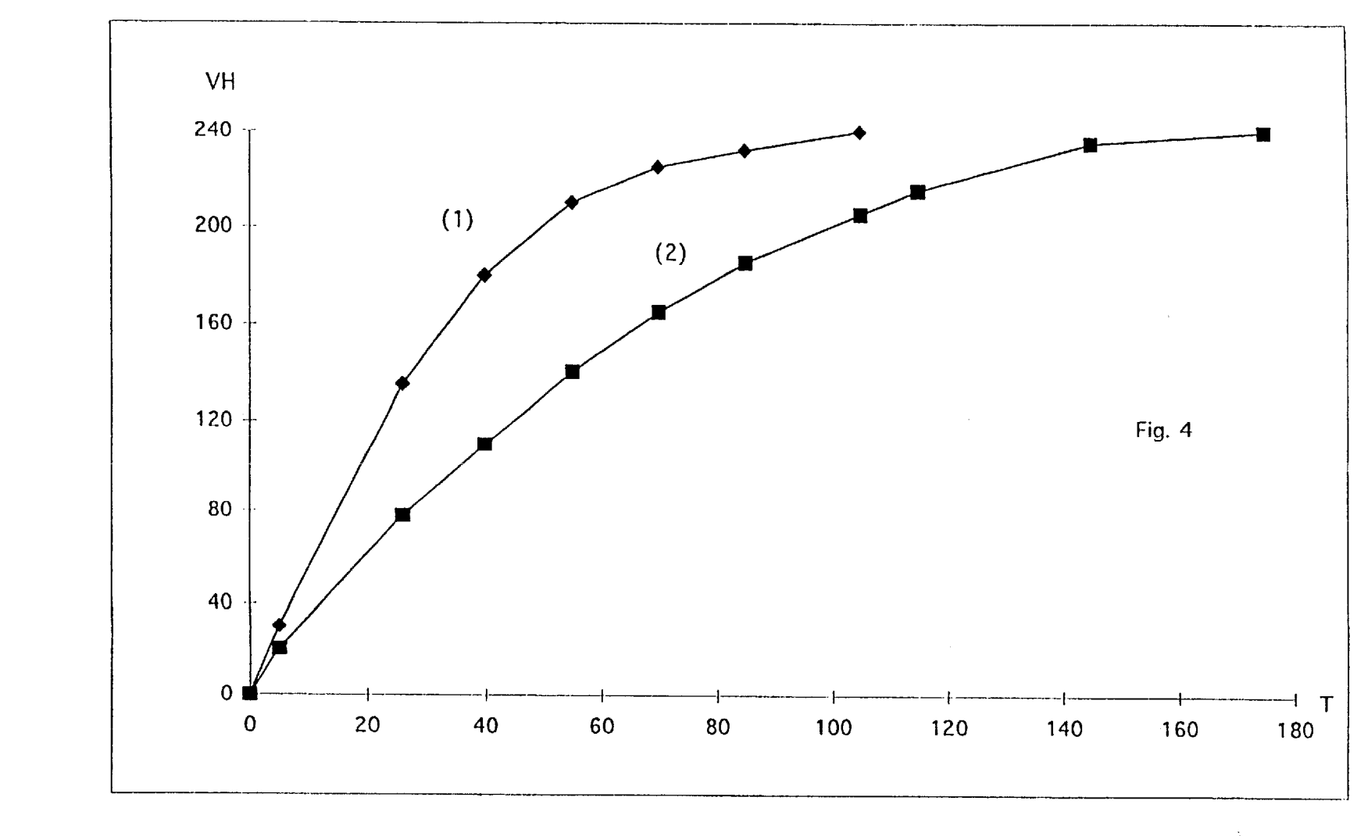
FIG. 4 of the Drawing graphically represents the variation in the volume of hydrogen consumed as a function of time during a cyclooctene hydrogenation reaction.

FIG. 4 represents the curve showing the variation in the volume of hydrogen consumed VH (expressed in ml) as a function of the time interval T (expressed in minutes) during a cyclooctene hydrogenation reaction catalyzed by AlNi particles (curve 1) and Ni particles (curve 2).

Figure 5:
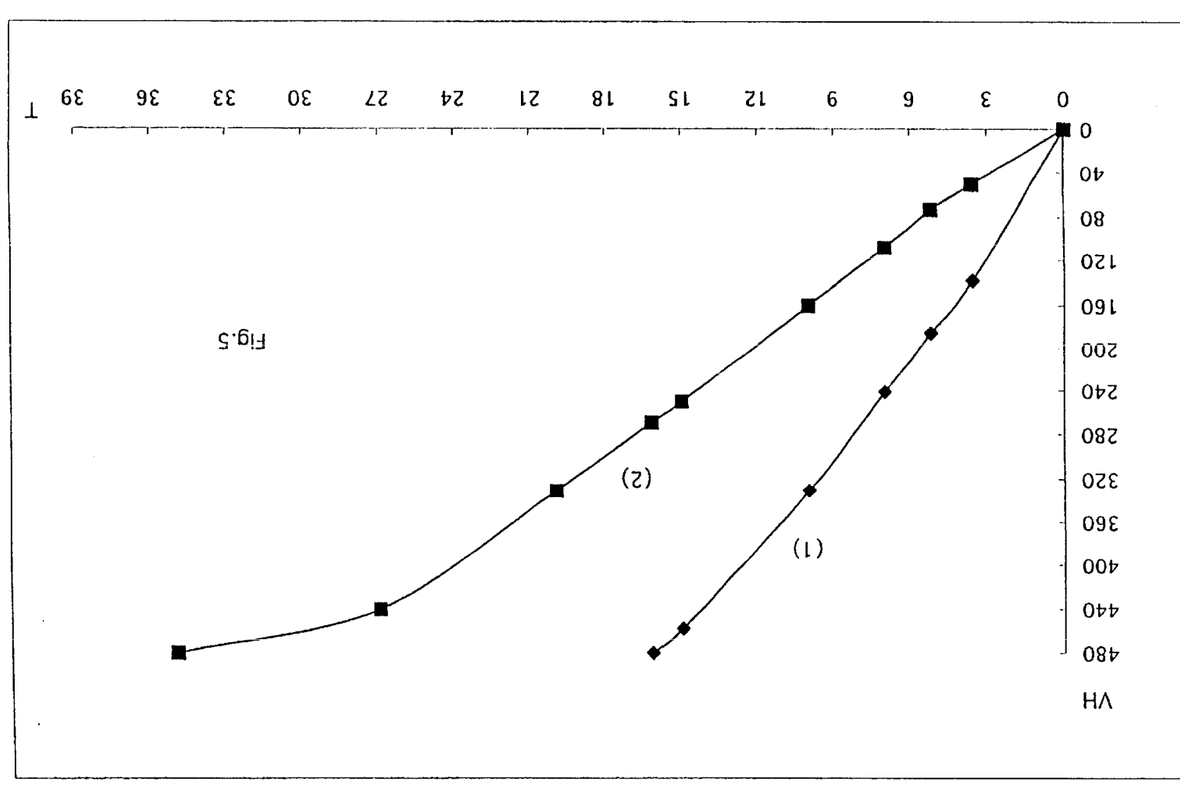
FIG. 5 of the Drawing graphically represents the variation in the volume of hydrogen consumed as a function of time during a diphenylacetylene hydrogenation reaction.

FIG. 5 represents the curve showing the variation in the volume of hydrogen consumed VH (expressed in ml) as a function of the time interval T (expressed in minutes) during a diphenylacetylene hydrogenation reaction catalyzed by AlNi particles (curve 1) and Ni particles (curve 2).

EXAMPLE 1

Preparation of Bimetallic Al—Ni [1/1] Particles 0.72 g (90 mmol) of LiH, 1.76 g (10 mmol) of nickel acetate $Ni(OAc)_2$ and 3.24 g (10 mmol) of aluminum acetylacetonate $Al(Acac)_3$ in suspension in 30 ml of THF were introduced, at a temperature of approximately 20° C. and under a nitrogen atmosphere, into a reactor equipped with a reflux condenser, a dropping funnel and a thermometer. The suspension obtained was brought to reflux (approximately 63° C.).

1.48 g (20 mmol) of t-BuOH, in solution in 10 ml of THF, were subsequently added dropwise over approximately 10 min via the dropping funnel. The suspension was subsequently stirred for 6 hours at 63° C.

The formation of the metallic particles was monitored by measuring the evolution of hydrogen resulting from the reaction in which t-BuOLi is formed and from the reduction of the metal salts. The change in the evolution of hydrogen is represented on curve 1 in FIG. 1.

After heating for 6 hours at 63° C., the particles are completely formed and exist in the form of a black-colored suspension.

EXAMPLE 2

Preparation of Bimetallic Al—Ni [2/1] Particles

The preparation was carried out in the same way as in Example 1 but by using 0.96 g (120 mmol) of LiH, 1.76 g (10 mmol) of $Ni(OAc)_2$ and 6.48 g (20 mmol) of $Al(Acac)_3$.

The time period for the heating at 63° C. with stirring was 10 hours. The change in the evolution of hydrogen is represented on curve 2 in FIG. 1.

EXAMPLE 3

Preparation of Trimetallic Al—Ni—Co [1/1/1] Particles

The preparation was carried out in the same way as in Example 1 but using 0.88 g (110 mmol) of LiH, 1.76 g (10 mmol) of $Ni(OAc)_2$, 1.76 g (10 mmol) of $Co(OAc)_2$ and 3.24 g (10 mmol) of $Al(Acac)_3$.

The time period for the heating at 63° C. with stirring was 12 hours. The change in the evolution of hydrogen is represented on curve 3 in FIG. 1.

EXAMPLE 4

Preparation of Bimetallic Al—Ni [1/1] Particles

The preparation was carried out in the same way as in Example 1 but using 2.16 g (90 mmol) of NaH, 1.76 g (10 mmol) of $Ni(OAc)_2$ and 3.24 g (10 mmol) of $Al(Acac)_3$.

The time period for the heating at 63° C. with stirring was 5 hours. The change in the evolution of hydrogen is represented on curve 1 in FIG. 2.

EXAMPLE 5

Preparation of Bimetallic Al—Ni [1/1] Particles

The preparation was carried out in the same way as in Example 1 but using 2.16 g (90 mmol) of NaH, 1.28 g (10 mmol) of $NiCl_2$ and 3.24 g (10 mmol) of $Al(Acac)_3$.

The time period for the heating at 63° C. with stirring was 6 hours. The change in the evolution of hydrogen is represented on curve 2 in FIG. 2.

EXAMPLE 6

Preparation of Bimetallic Al—Ni [1/1] Particles

The preparation was carried out in the same way as in Example 1 but using 2.16 g (90 mmol) of NaH, 2.57 g (10 mmol) of $Ni(Acac)_2$ and 3.24 g (10 mmol) of $Al(Acac)_3$.

The time period for the heating at 63° C. with stirring was 5 hours. The change in the evolution of hydrogen is represented on curve 3 in FIG. 2.

EXAMPLE 7

Preparation of Bimetallic Al—Ni [1/1] Particles

The preparation was carried out in the same way as in Example 1 but using 2.16 g (90 mmol) of NaH, 2.57 g (10 mmol) of $Ni(Acac)_2$ and 1.33 g (10 mmol) of $AlCl_3$.

The time period for the heating at 63° C. with stirring was 5 hours.

EXAMPLE 8

Preparation of Bimetallic Al—Ni [1/1] Particles

The preparation was carried out in the same way as in Example 6 but using 1.92 g (80 mmol) of NaH, 2.75 g (10 mmol) of $Ni(Acac)_2$, 3.24 g (10 mmol) of $Al(Acac)_3$ and 0.74 g (10 mmol) of t-BuOH.

The time period for the heating at 63° C. with stirring was 3 hours.

EXAMPLE 9

Preparation of Bimetallic Al—Ni [1/1] Particles

The preparation was carried out in the same way as in Example 6 but using 2.28 g (95 mmol) of NaH, 2.57 g (10 mmol) of $Ni(Acac)_2$, 3.24 g (10 mmol) of $Al(Acac)_3$ and 1.85 g (25 mmol) of t-BuOH.

The time period for the heating at 63° C. with stirring was 2 hours.

EXAMPLE 10

Preparation of Bimetallic Al—Ni [1/1] Particles

The preparation was carried out in the same way as in Example 4 but adding 3.12 g (20 mmol) of 2,2'-bipyridine to the starting suspension of hydride and of metal salts.

The time period for the heating at 63° C. with stirring was 3 hours.

The specific conditions for each of the above examples are collated in the following Table 1:

TABLE 1

| Ex | Precursors | mmol | Hydride | mmol | Alkoxyde | mmol | Solvent | temp. | Time period |
|---|---|---|---|---|---|---|---|---|---|
| 1 | Ni(OAc)$_2$ | 10 | LiH | 90 | t-BuOLi | 20 | THF | 63° C. | 6 h |
|   | Al(Acac)$_3$ | 10 |  |  |  |  |  |  |  |
| 2 | Ni(OAc)$_2$ | 10 | LiH | 120 | t-BuOLi | 20 | THF | 63° C. | 10 h |
|   | Al(Acac)$_3$ | 20 |  |  |  |  |  |  |  |
| 3 | Ni(OAc)$_2$ | 10 | LiH | 110 | t-BuOLi | 20 | THF | 63° C. | 12 h |
|   | Co(OAc)$_2$ | 10 |  |  |  |  |  |  |  |
|   | Al(Acac)$_3$ | 10 |  |  |  |  |  |  |  |
| 4 | Ni(OAc)$_2$ | 10 | NaH | 90 | t-BuOLi | 20 | THF | 63° C. | 5 h |
|   | Al(Acac)$_3$ | 10 |  |  |  |  |  |  |  |
| 5 | NiCl$_2$ | 10 | NaH | 90 | t-BuOLi | 20 | THF | 63° C. | 6 h |
|   | Al(Acac)$_3$ | 10 |  |  |  |  |  |  |  |
| 6 | Ni(Acac)$_2$ | 10 | NaH | 90 | t-BuOLi | 20 | THF | 63° C. | 5 h |
|   | Al(Acac)$_3$ | 10 |  |  |  |  |  |  |  |
| 7 | Ni(Acac)$_2$ | 10 | NaH | 90 | t-BuOLi | 20 | THF | 63° C. | 5 h |
|   | AlCl$_3$ | 10 |  |  |  |  |  |  |  |
| 8 | Ni(Acac)$_2$ | 10 | NaH | 80 | t-BuOLi | 10 | THF | 63° C. | 3 h |
|   | Al(Acac)$_3$ | 10 |  |  |  |  |  |  |  |
| 9 | Ni(Acac)$_2$ | 10 | NaH | 95 | t-BuOLi | 25 | THF | 63° C. | 2 h |
|   | Al(Acac)$_3$ | 10 |  |  |  |  |  |  |  |
| 10 | Ni(OAc)$_2$ | 10 | NaH | 90 | t-BuOLi | 20 | THF | 63° C. | 3 h |
|   | Al(Acac)$_3$ | 10 |  |  |  | bipyridine | 20 |  |  |  |

EXAMPLE 11

The particles obtained by the process of Example 1 were characterized by transmission electron microscopy using a Philips CM20/STEM microscope. The characterization showed that the size of the ultrafine particles obtained is of the order of a nanometer.

Energy dispersion X-ray microanalysis, carried out on Al—Ni samples, showed that there exists a homogeneous distribution (at the 100 nm scale) of the Al and Ni metallic species. Quantitative analysis based on making use of the X-ray signals emitted during inelastic scattering with high energy transfer shows that the composition of the metallic elements is 50/50 by number of atoms.

The progress of the reaction was determined by measuring the hydrogen absorbed. The hydrogen absorption kinetics are represented in FIGS. 3, 4 and 5.

The curves 1 and 2 in FIG. 3 correspond respectively to Examples 12 and 13.

The curves 1 and 2 in FIG. 4 correspond respectively to Examples 14 and 15.

The curves 1 and 2 in FIG. 5 correspond respectively to Examples 16 and 17.

The yield of hydrogenated product formed over time was determined by quantitative gas chromatographic analysis of the aliquots withdrawn. The yields are expressed as molar percentage.

The reaction conditions for the different examples are given in the following Table 2.

TABLE 2

| | | | | | | Result | | |
|---|---|---|---|---|---|---|---|---|
| Example | S | Cat. | V(ml) | % Ni | RP | $t_{50\%}$ (min) | $t_{90\%}$ (min) | $t_{100\%}$ (min) |
| 12 | styrene | Ni—Al | 0.5 | 0.625 | ethylbenzene | 4.5 | 17 | 20 |
| 13 | styrene | Ni | 0.5 | 0.625 | ethylbenzene | 21 | 38 | 45 |
| 14 | cyclooctene | Ni—Al | 4 | 5 | cyclo-octane | 24 | 66 | 105 |
| 15 | cyclooctene | Ni | 4 | 5 | cyclo-octane | 45 | 123 | 175 |
| 16 | diphenylacetylene | Ni—Al | 1.5 | 1.875 | diphenylethane | 7 | 15 | 16 |
| 17 | diphenylacetylene | Ni | 3 | 3.75 | diphenylethane | 14 | 26 | 35 |

EXAMPLES 12 to 17

Examples 12, 14 and 16 relate to a hydrogenation reaction catalyzed by polymetallic particles obtained according to Example 4 hereinabove.

Examples 13, 15 and 17 relate to a hydrogenation reaction carried out under conditions strictly identical to those of Examples 12, 14 and 16 using monometallic Ni particles obtained by Brunet et al., Journal of Organic Chemistry, 1980, vol. 45, pp. 1937–1945.

In all cases, the hydrogenation reaction was carried out in equipment conventional for a hydrogenation at atmospheric pressure. The operating conditions were as follows:
  substrate to be hydrogenated: 20 mmol
  hydrogen pressure: 1 bar (=10$^5$ Pa)
  solvent: 15 ml of ethanol.

S: substrate to be hydrogenated

V: volume of suspension used as catalyst (resulting from Example 4 for Examples 12, 14 and 16; resulting from the process described in Brunet, previously cited, for Examples 13, 15 and 17)

% Ni: molar percentage of nickel in the reaction medium

RP: reaction product $t_{50\%}$: time period, expressed in minutes, needed to obtain a molar yield of 50%.

$t_{90\%}$: time period, expressed in minutes, needed to obtain a molar yield of 90%.

$t_{100\%}$: time period, expressed in minutes, needed to obtain a molar yield of 100%.

It is apparent that, for hydrogenation reactions, the time periods needed to obtain a given yield are greatly reduced, indeed even approximately halved, when a monometallic catalyst is replaced by a polymetallic catalyst.

EXAMPLES 18 to 27

Examples 18, 20, 22, 24 and 26 relate to a direct coupling reaction of halogenated aromatic derivatives catalyzed by polymetallic particles obtained according to Example 10 hereinabove.

Examples 19, 21, 23, 25 and 27 relate to a direct coupling reaction of halogenated aromatic derivatives carried out under conditions strictly identical to those of Example 18, 20, 22, 24 and 26 using monometallic particles obtained according to Lourak et al., Journal of Organic Chemistry, 1989, vol. 54, pp. 4840–4844, that is to say a monometallic nickel system.

The procedure used for each of Examples 18 to 27 is as follows: the halogenated aromatic derivative, in solution in 10 ml of THF, was added dropwise to the suspension of particles which is obtained in Example 10, for Examples 18, 20, 22, 24 and 26, and to the suspension of particles which is obtained according to the Lourak process hereinabove, for Examples 19, 21, 23, 25 and 27. The amounts of halogenated derivative used are shown in Table 3 hereinbelow.

The yield of coupling product formed over time was determined by quantitative gas chromatographic analysis from the aliquots withdrawn. The yields obtained are expressed as molar percentage, on the one hand with respect to the starting halogenated derivative and, on the other hand, with respect to the amount of nickel used.

TABLE 3

| Ex. | ArX | Amount ArX (mmol) | Reaction time (h) | Reaction product | Yd with respect to ArX | Yd with respect to Ni |
|---|---|---|---|---|---|---|
| 18 | bromobenzene | 40 | 0.75 | biphenyl | 85 | 340 |
| 19 | bromobenzene | 20 | 1.75 | biphenyl | 80 | 160 |
| 20 | 2-methyl-bromobenzene | 20 | 0.75 | 2,2'-dimethyl-biphenyl | 85 | 170 |
| 21 | 2-methyl-bromobenzene | 10 | 0.5 | 2,2'-dimethyl-biphenyl | 90 | 90 |
| 22 | 3-methyl-bromobenzene | 40 | 1.25 | 3,3'-dimethyl-biphenyl | 64 | 256 |
| 23 | 3-methyl-bromobenzene | 20 | 1.5 | 3,3'-dimethyl-biphenyl | 50 | 100 |
| 24 | 4-methyl-bromobenzene | 40 | 0.5 | 4,4'-dimethyl-biphenyl | 87 | 348 |
| 25 | 4-methyl-bromobenzene | 40 | 21 | 4,4'-dimethyl-biphenyl | 71 | 284 |
| 26 | 2-methyl-bromobenzene | 20 | 0.3 | 4,4'-dimethyl-biphenyl | 99 | 198 |
| 27 | 2-methyl-bromobenzene | 20 | 1 | 4,4'-dimethyl-biphenyl | 67 | 134 |

It is apparent that, for coupling reactions, the yields are increased in variable proportions according to the tests, with generally shorter reaction times.

What is claimed is:

1. Process for the preparation of nanometric polymetallic particles by reduction of a mixture of salts in solution in an organic solvent, comprising contacting the mixture with an alkali metal or alkaline earth metal hydride at a temperature of less than or equal to the reflux temperature of the solvent, wherein the mixture of salts in solution comprises at least one salt of a metal having a standard oxidation potential $E°_{M^{n+}/M}$ at 25° C. of greater than −1.18 V and wherein an alkali metal, alkaline earth metal or transition metal alkoxide or an alkali metal, alkaline earth metal or transition metal aminoalkoxide is added to the mixture of salts in solution in the organic solvent.

2. Process according to claim 1, wherein the mixture of salts which is reacted with the alkali metal or alkaline earth metal hydride comprises at least one salt of a metal having a standard oxidation potential $E°_{M^{n+}/M}$ at 25° C. of less than −1.20 V.

3. Process for hydrogenating olefins, comprising contacting olefins with a material obtained by the process according to claim 2.

4. Process according to claim 2, wherein the metal of the salt of a metal having a standard oxidation potential $E°_{M^{n+}/M}$ at 25° C. of less than −1.20 V is chosen from the group consisting of Zr, Ce, Ti, Hf and Al.

5. Process according to claim 1, wherein the salts are chosen from the group consisting of halides, organic acid salts and alkoxides.

6. Process according to claim 5, wherein the organic acid salt is an acetate or an acetylacetonate.

7. Process for hydrogenating olefins, comprising contacting olefins with a material obtained by the process according to claim 6.

8. Process for hydrogenating olefins, comprising contacting olefins with a material obtained by the process according to claim 5.

9. Process according to claim 1, wherein the metal of the salt of a metal having a standard oxidation potential $E°_{M^{n+}/M}$ at 25° C. of greater than −1.18 V is chosen from group consisting of Ni, Co, Fe, Cu, Zn, Cd, Cr, Mn, Pd, Ag, Pt, Au, Bi and Sb.

10. Process according to claim 1, wherein the alkali metal hydride is chosen from the group consisting of sodium hydride, lithium hydride and potassium hydride.

11. Process according to claim 1, wherein the alkaline earth metal hydride is calcium hydride or magnesium hydride.

12. Process according to claim 1, wherein the alkoxide is chosen from sodium tert-butoxide, lithium tert-butoxide and aluminum isopropoxide and the aminoalkoxide is sodium N,N-dimethylaminoethoxide.

13. Process according to claim 12, wherein the alkoxide is formed in situ by the action of the hydride on an aliphatic or aromatic alcohol.

14. Process according to claim 13, wherein the alcohol is chosen from the group consisting of tert-butanol, 2-methyl-2-pentanol, phenol, diethylene glycol monoethyl ether, neopentane, cyclohexanol, ethanol and isopropanol.

15. Process according to claim 1, wherein the reaction in which the mixture of salts is reduced is carried out at a temperature within the range limited by the solidifying temperature and by the reflux temperature of the solvent used.

16. Process according to claim 1, wherein a compound comprising a nitrogen-comprising or phosphorus-comprising ligand is added to the mixture of salts in solution in the organic solvent.

17. Process according to claim 16, wherein a compound comprising a nitrogen-comprising ligand is chosen from the group consisting of bipyridines and terpyridines.

18. Process for coupling halogenated aromatic derivatives, comprising contacting halogenated aromatic derivatives with the material obtained by the process of claim 17.

19. Process according to claim 16, wherein the compound comprising a phosphorus-comprising ligand is chosen from the group consisting of triphenylphosphine, 1,2-bis(diphenylphosphino)ethane, alkylphosphines and arylphosphines.

20. Process for coupling halogenated aromatic derivatives, comprising contacting halogenated aromatic derivatives with the material obtained by the process of claim 19.

21. Process for coupling halogenated aromatic derivatives, comprising contacting halogenated aromatic derivatives with a material obtained by the process of claim 16.

22. Process for hydrogenating olefins, comprising contacting olefins with a material obtained by the process according to claim 1.

23. Material comprising nanometric polymetallic particles having a mean crystallite dimension of less than 4 nm and an intimate association of the various metals present inside the grains, at least one of the metals constituting said particles being a metal having a standard oxidation potential $E°_{M^{n+}/M}$ at 25° C. of greater than −1.18 V and at least one of the metals constituting said particles being a metal having a standard oxidation potential $E°_{M^{n+}/M}$ at 25° C. of less than −1.20 V.

24. Material according to claim 23, wherein the metal having a standard oxidation potential $E°_{M^{n+}/M}$ at 25° C. of less than −1.20 V is chosen from the group consisting of Zr, Ce, Ti, Hf and Al.

25. Material according to claim 23, wherein the metal having a standard oxidation potential $E°_{M^{n+}/M}$ at 25° C. of greater than −1.18 V is chosen from the group consisting of Ni, Co, Fe, Cu, Zn, Cd, Cr, Mn, Pd, Ag, Pt, Au, Bi and Sb.

26. The material according to claim 23, wherein the nanometric polymetallic particles are suspended in a liquid, and wherein the particles have a mean particle size of less than 4 nm.

27. The material according to claim 23, wherein the material is effective for catalyzing a hydrogenation reaction or a reaction of coupling halogenated aromatic derivatives.

* * * * *